(12) United States Patent
Hong et al.

(10) Patent No.: US 9,926,283 B2
(45) Date of Patent: Mar. 27, 2018

(54) INTERMEDIATE COMPOUND FOR PREPARING ROSUVASTATIN CALCIUM AND METHOD FOR PREPARING ROSUVASTATIN CALCIUM THEREFROM

(71) Applicants: Asymchem Laboratories (Tianjin) Co., Ltd., Tianjin (CN); Asymchem Life Science (Tianjin) Co., Ltd., Tianjin (CN); Tianjin Asymchem Pharmaceutical Co., Ltd., Tianjin (CN); Asymchem Laboratories (Fuxin) Co., Ltd., Liaoning (CN); Jilin Asymchem Laboratories Co., Ltd., Jilin (CN)

(72) Inventors: Hao Hong, Tianjin (CN); James Gage, Tianjin (CN); Jiuyuan Li, Tianjin (CN); Litao Shen, Tianjin (CN); Lei Zhang, Tianjin (CN); Changming Dong, Tianjin (CN)

(73) Assignees: Asymchem Laboratories (Tianjin) Co., Ltd., Tianjin (CN); Asymchem Life Science (Tianjin) Co., Ltd., Tianjin (CN); Tianjin Asymchem Pharmaceutical Co., Ltd., Tianjin (CN); Asymchem Laboratories (Fuxin) Co., Ltd., Liaoning (CN); Jilin Asymchem Laboratories Co., Ltd., Jilin (CN)

( * ) Notice: Subject to any disclaimer, the term of this patent is extended or adjusted under 35 U.S.C. 154(b) by 0 days.

(21) Appl. No.: 15/124,083

(22) PCT Filed: Mar. 7, 2014

(86) PCT No.: PCT/CN2014/073079
§ 371 (c)(1),
(2) Date: Sep. 7, 2016

(87) PCT Pub. No.: WO2015/131405
PCT Pub. Date: Sep. 11, 2015

(65) Prior Publication Data
US 2017/0022169 A1    Jan. 26, 2017

(51) Int. Cl.
*C07D 239/42* (2006.01)
*C07F 9/6512* (2006.01)

(52) U.S. Cl.
CPC ........ *C07D 239/42* (2013.01); *C07F 9/65122* (2013.01); *C07B 2200/13* (2013.01); *Y02P 20/55* (2015.11)

(58) Field of Classification Search
CPC ......................... C07D 239/42; C07F 9/65122
USPC .................................................. 544/243, 330
See application file for complete search history.

(56) References Cited

U.S. PATENT DOCUMENTS

2005/0124639 A1    6/2005    Joshi et al.

FOREIGN PATENT DOCUMENTS

| CN | 102351901 A | 2/2012 |
| CN | 102643302 A | 8/2012 |
| CN | 103804414 A | 5/2014 |
| EP | 0521471 A1 | 10/2001 |
| JP | 2003518474 A | 6/2003 |
| WO | 2004103977 A2 | 12/2004 |

OTHER PUBLICATIONS

Nritten Opinion of the International Search Authority for PCT/CN2014/073079; dated Jul. 9, 2016.
Translation of the International Search Report for PCT/CN2014/073079; dated Nov. 9, 2015.
Upadhyay, Puspech K. et al., "A facile synthesis of 5,6-dihydro-5-hydroxy-2 (1H)-pyridone," Tetrahedron Letters 50, (2009), pp. 2440-2442.
Japanese Office Action for corresponding Japan Patent Application No. 2016-572868 (dated Jun. 19, 2017), 3 pages.

*Primary Examiner* — Deepak R Rao
(74) *Attorney, Agent, or Firm* — Calfee, Halter & Griswold LLP

(57) ABSTRACT

Provided are an intermediate compound for preparing rosuvastatin calcium and a preparation method of the rosuvastatin calcium. The method comprises: using the foregoing intermediate compound as a raw material, and subjecting the raw material to a step of Wittig reaction, a step of protecting group removal and hydrolysis and a step of calcium salt formation, so as to obtain the rosuvastatin calcium. The product, which is prepared from the intermediate compound, can be substantially enhanced in stereoselectivity and also notably improved in purity and yield; in addition, the method for preparing rosuvastatin calcium from the intermediate compound is simple, convenient and low in cost.

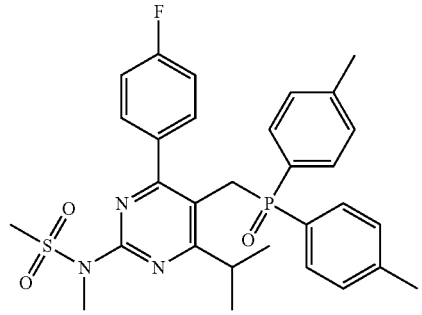

10 Claims, No Drawings

INTERMEDIATE COMPOUND FOR PREPARING ROSUVASTATIN CALCIUM AND METHOD FOR PREPARING ROSUVASTATIN CALCIUM THEREFROM

CROSS-REFERENCE TO RELATED APPLICATIONS

The present application is the US national phase of PCT application PCT/CN2014/073079, filed on Mar. 7, 2014 with the title "Intermediate Compound for Preparing Rosuvastatin Calcium and Method for Preparing Rosuvastatin Calcium Therefrom."

TECHNICAL FIELD

The present application relates to the field of synthesis of pharmaceuticals and pharmaceutical intermediates, and specifically relates to an intermediate compound which may be used for the preparation of rosuvastatin calcium, and a method for preparing rosuvastatin calcium from said intermediate compound.

TECHNICAL BACKGROUND

Rosuvastatin calcium is a selective inhibitor of HMG-CoA reductase. It was developed by AstraZeneca company, and has been marketed in many countries and regions including the United States, Japan, Europe and China, with the trade name "CRESTOR" (trade name in Chinese: KeDing). It has a chemical name of calcium bis[(E)-7-[4-(4-fluorophenyl)-6-isopropyl-2-[methyl(methylsulfonyl)amino]pyrimidin-5-yl](3R,5S)-3,5-dihydroxy-hept-6-enoate], and has a structure of formula A. Rosuvastatin calcium is a highly effective hypolipidemic drug, and can be used for treating primary hypercholesterolemia and mixed type lipodystrophy as well as homozygous familial hypercholesterolemia. It is highly favored due to its advantages of high efficiency and low toxic side effects, and therefore has a very broad prospect.

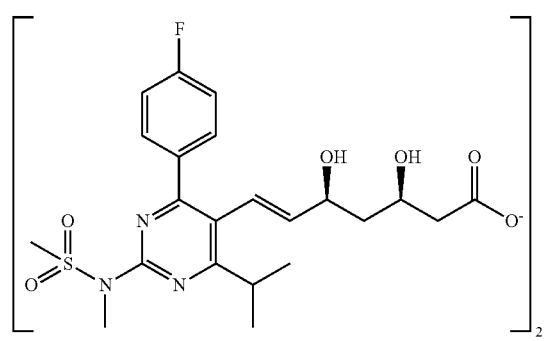

A

Currently there have been many patent documents reporting the synthetic processes of rosuvastatin calcium and the preparation of the key intermediates. The processes can be generally classified into the following two categories: (1) introducing an aldehyde group to the pyrimidine core, making the side chain as a Wittig reagent, obtaining the trans olefin intermediate via Wittig reaction, which is further converted to the product; (2) introducing a Ylide reagent or other reagents to the pyrimidine core, making the side chain as an aldehyde compound, obtaining the trans olefin intermediate via Wittig reaction, which is further converted to the product. Several processes suitable for industrial production are summarized below.

Patent application WO 2004103977A reports that the key trans intermediate, compound 3, is obtained with a selectivity of about 50:1 through olefination reaction of compound 1 with the side chain aldehyde in the presence of an alkali. Compound 3 is subjected to deprotection, hydrolysis and calcium salt formation to give rosuvastatin calcium. The patent application also seeks protection of the key starting material and the intermediates 1 and 3.

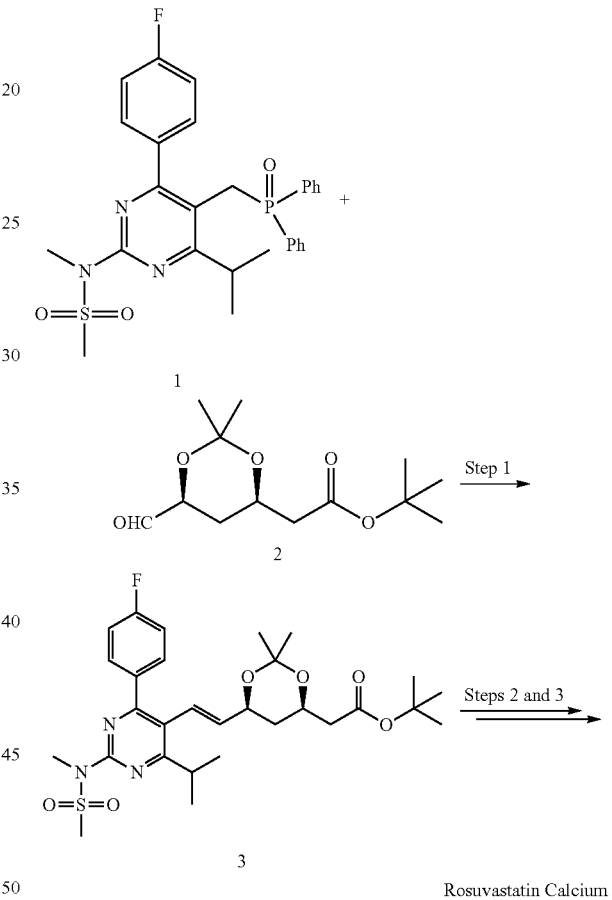

Patent application US 2005/0124639A1 reports conducting the olefination reaction of the quaternary phosphonium compound 4 with the aldehyde side chain 5, and obtaining the key trans intermediate compound 6 with a medium selectivity. Compound 6 is subjected to deprotection, hydrolysis and calcium salt formation to give rosuvastatin calcium, wherein $R^1$, $R^2$ and $R^3$ in the quaternary phosphonium may be alkyl or aromatic groups, and the anion may be halogen, trifluoroacetyl, methylsulfonyl or the like. The patent application also seeks protection of the key starting material 4.

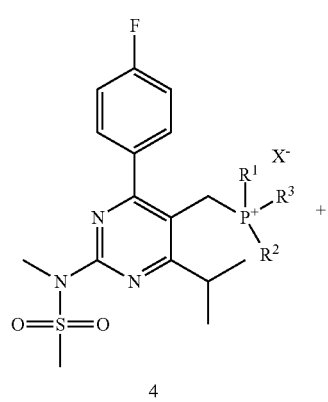

4

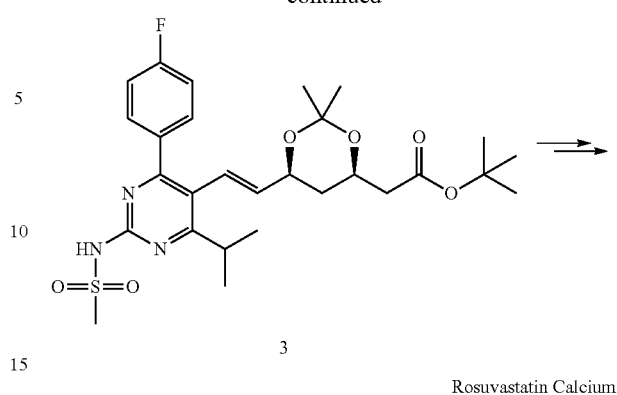

Rosuvastatin Calcium

Patent application EP 0521471A1 reports the preparation of rosuvastatin calcium from pyrimidine aldehyde compound 8 and compound 9 through the steps of Wittig reaction, deprotection, selective reduction and hydrolysis. Patent application CN 200510026350 makes further improvements to said process.

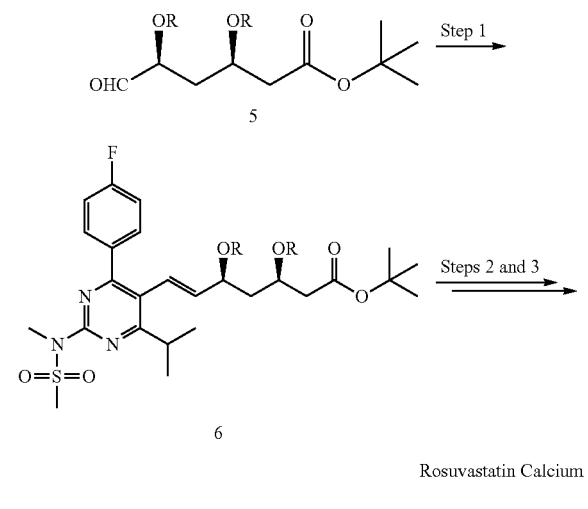

Rosuvastatin Calcium

Patent application WO 2010023678 reports obtaining the key intermediate compound 3 through Julia olefination reaction of raw material 7 with compound 2, and then obtaining rosuvastatin calcium through a similar process.

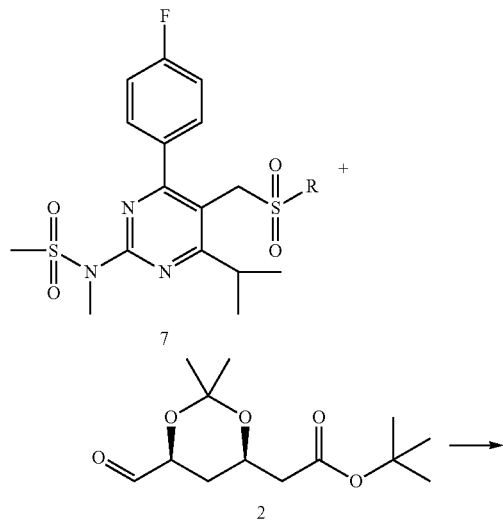

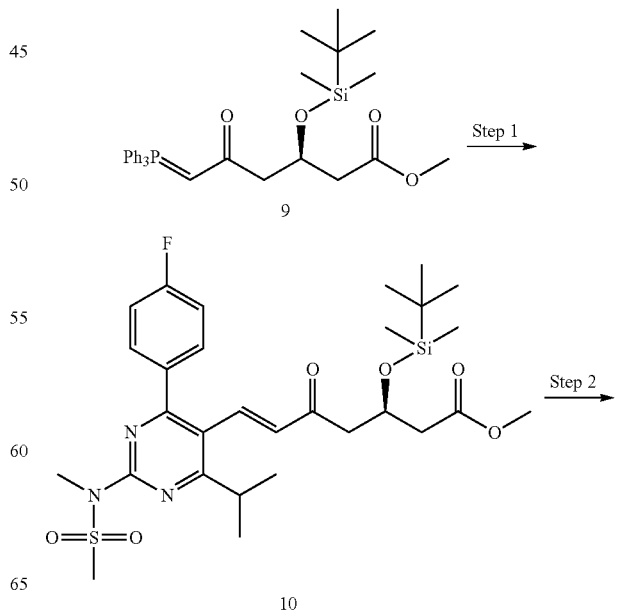

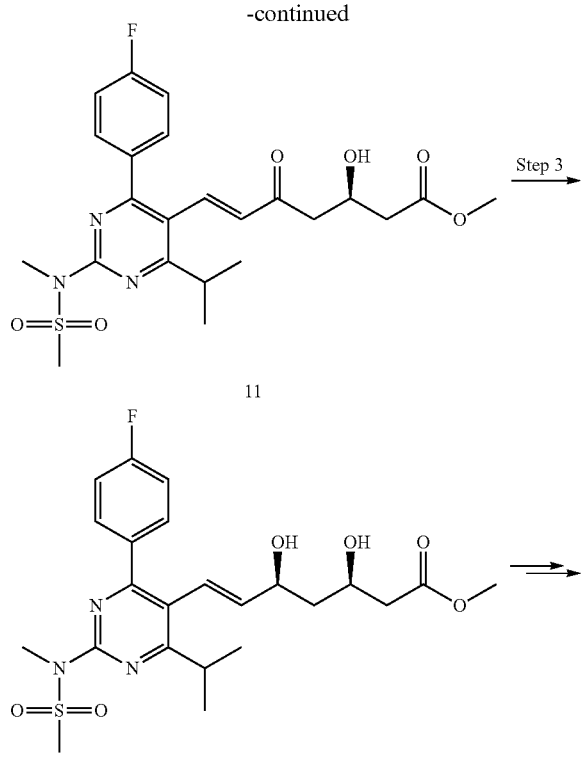

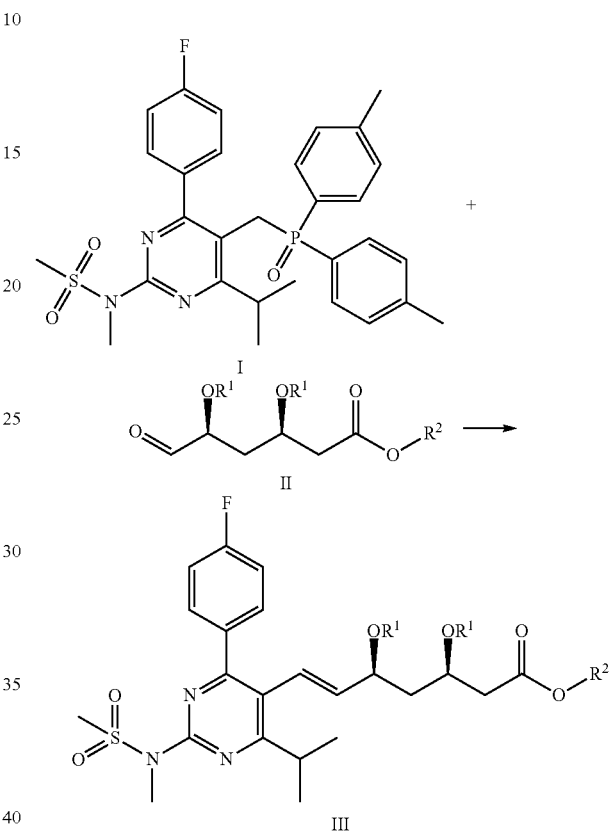

Although rosuvastatin calcium can be industrially produced by the above routes, there are still problems in many aspects such as synthesis of raw materials, selectivity of the reactions, separation and purification of the intermediates and the final products. Accordingly, it is very necessary to develop a preparation method with low costs, simple operations, and high product qualities.

SUMMARY OF THE INVENTION

To overcome the problems of low selectivity and high costs in the synthesis of rosuvastatin calcium, one object of the present application is to provide an intermediate compound for the preparation of rosuvastatin calcium.

Another object of the present application is to provide a method for preparing rosuvastatin calcium.

The intermediate compound provided in the present application for the preparation of rosuvastatin calcium has a structure of formula (I).

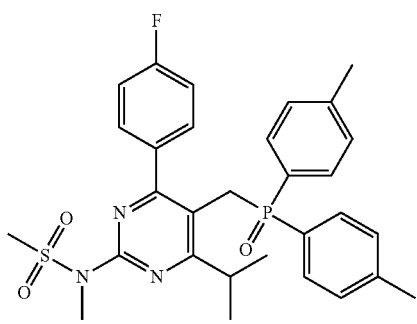

In the method provided in the present application for preparing rosuvastatin calcium, the intermediate compound in the above technical solution is used as a starting material, which firstly undergoes Wittig reaction with the compound of formula (II) to give the intermediate compound of formula (III), which is then subjected to steps of deprotection and hydrolysis and salt formation to give said rosuvastatin calcium.

In formulae (II) and (III), $R^1$ represents TBS, TES or TIPS protecting group, or two $OR^1$ groups form a structure of

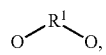

in which $R^1$ represents isopropyl; $R^2$ represents C4~C10 alkyl.

In one embodiment, $R^2$ represents tert-butyl, tert-pentyl, cyclopentyl or cyclohexyl.

In the above preparation method, the Wittig reaction process comprises: adding the intermediate compound of claim 1 into an organic solvent, cooling down to −80~−20° C., then adding an alkali, adding dropwise a solution of the compound of formula (II) at −80~−20° C., reacting at −80~−20° C. for 1~3 hours after the addition is completed, warming up to −45~25° C. and reacting until the reaction is completed, quenching the reaction, extracting, concentrating the extraction solution, and adding a solvent to the crude product obtained by concentrating, which leads to crystallization to give the intermediate compound of formula (III).

In one embodiment, the alkali is selected from the group consisting of sodium hydride, butyllithium, lithium diisopropylamide, lithium hexamethyldisilazide, sodium hexamethyldisilazide, 2,2,6,6-tetramethylpiperidinylmagnesium chloride (CAS: 215863-85-7), 2,2,6,6-tetramethylpiperidine lithium, potassium hexamethyldisilazide, lithium isopropylphenylamide and sodium isopropylphenylamide; and the molar ratio of the alkali to the above intermediate compound of formula (I) is 0.9~2.0:1, preferably 1.1:1.

In one embodiment, the organic solvent is selected from the group consisting of 1,4-dioxane, tetrahydrofuran, 2-methyltetrahydrofuran, N,N-dimethylformamide, methyl tert-butyl ether, ethylene glycol dimethyl ether, and a mixture of two of them in any ratio, preferably tetrahydrofuran; and the amount of the organic solvent is 5~20 mL/g relative to the above intermediate compound of formula (I).

In one embodiment, the molar ratio of the above intermediate compound of formula (I) to the compound of formula (II) is 1:1~2, preferably 1:1.2.

In one embodiment, the solvent for extraction is selected from the group consisting of ethyl acetate, ethyl ether, methyl tert-butyl ether, n-heptane, toluene, dichloromethane, and a mixture thereof in any ratio, preferably n-heptane or toluene; and the amount of the solvent is 5~40 mL/g relative to the above intermediate compound of formula (I).

In one embodiment, the solvent for crystallization is selected from the group consisting of methanol, ethanol and isopropanol, preferably methanol; and the amount of the solvent is 2~20 mL/g relative to the above intermediate compound of formula (I).

In the above preparation method, after the intermediate compound of formula (III) is obtained at the end of Wittig reaction, an acid is added to the intermediate compound of formula (III) to conduct the deprotection reaction, followed by adding an alkali to conduct the hydrolysis reaction to give the compound of formula (IV), and then adding a calcium salt to the compound of formula (IV) to conduct the salt formation reaction to give rosuvastatin calcium.

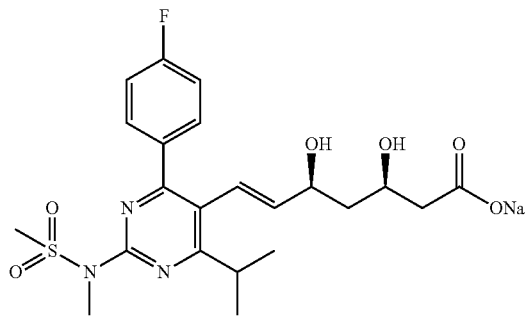

IV

In one embodiment, the acid is hydrochloric acid having a mass percentage concentration of 0.02~10%, the alkali is selected from the group consisting of an aqueous solution of sodium hydroxide, potassium hydroxide, potassium carbonate, sodium carbonate, potassium tert-butoxide, and a mixture thereof in any ratio.

In one embodiment, the calcium salt is selected from the group consisting of an aqueous solution of calcium chloride, calcium nitrate and calcium acetate having a mass percentage concentration of 3~20%.

In comparison with existing similar intermediates, both the stereo-selectivity and the yield of the resultant olefin product, i.e. the intermediate of formula (III), are significantly improved by using the intermediate compound of the present application, with a stereo-selectivity E/Z>99:1. The purity and the yield can also be significantly improved, and the purification step can also be effectively simplified. In addition, the method for preparing the intermediate compound of the present application is simple with low costs, and the intermediate compound is easy to obtain.

Due to the use of the above intermediate compound, the method for preparing rosuvastatin calcium as provided in the present application leads to significantly improved stereo-selectivity, purity and yield of the intermediate product, simple overall process, and significantly reduced costs, and therefore has a prospect of large-scale industrial application.

SPECIFIC EMBODIMENTS

In order to make the object, the technical solution and the advantages of the present application more clear, the technical solutions of exemplary embodiments of the present application will be further described hereinbelow.

One aspect of the present application provides an intermediate compound for preparing rosuvastatin calcium, which has the structure of formula (I).

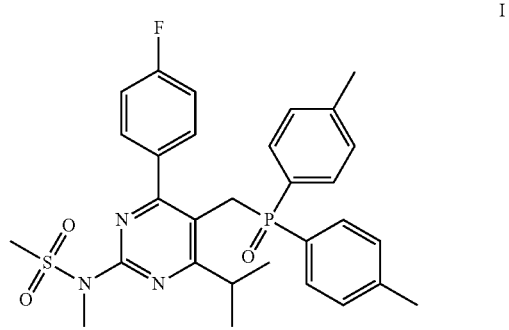

I

Said intermediate compound has a chemical name of N-(5-(4,4'-tolylphosphono)-methyl)-4-(4-fluorophenyl)-6-isopropylpyrimidin-2-yl)-N-methyl methanesulfonamide. In comparison with existing similar intermediate compounds, due to the hyperconjugative effect between methyl and phenyl and the change in the steric hindrance, using the intermediate of the present application leads to significant improvements in the yield and the stereo-selectivity of the resultant olefin product.

The above intermediate compound is prepared from commercially available 4-(4-fluorophenyl)-6-isopropyl-2-[(N-methyl-N-methanesulfonyl)amino]pyrimidine-5-methanol (compound V, CAS: 147118-36-3) via two-step reaction, i.e. bromination and coupling with the compound (VII).

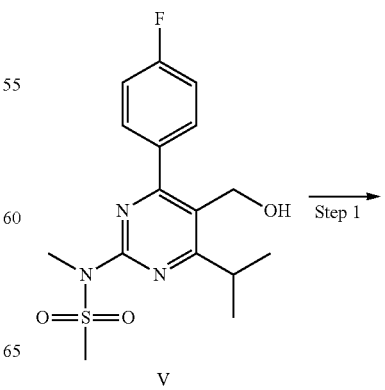

V

-continued

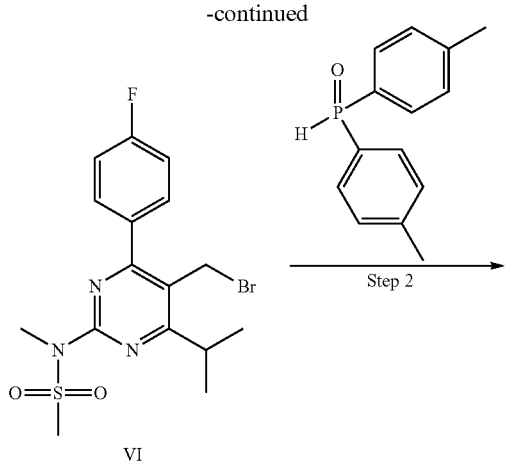

VI

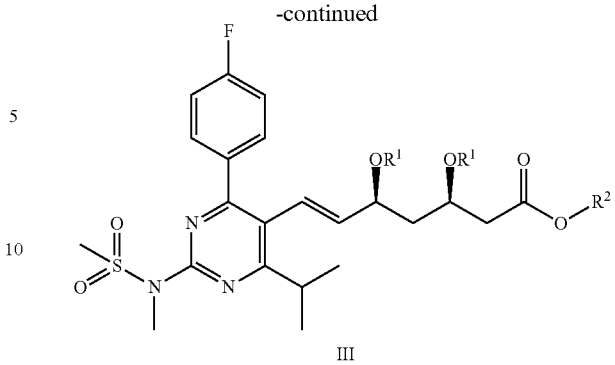

Step 2

-continued

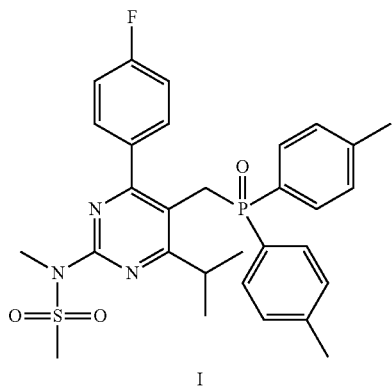

III

In formula (II) and formula (III), $R^1$ represents TBS, TES or TIPS protecting group, or two $OR^1$ groups form a structure of

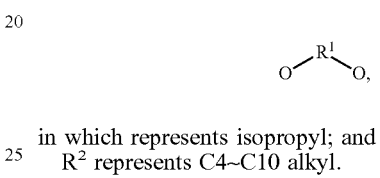

in which represents isopropyl; and
$R^2$ represents C4~C10 alkyl.

In one embodiment of the preparation method according to the present application, $R^2$ may represent tert-butyl, tert-pentyl, cyclopentyl or cyclohexyl.

Specifically, the preparation method of the present application includes the following steps.

(1) N-(5-((4,4'-tolylphosphono)-methyl)-4-(4-fluorophenyl)-6-isopropylpyrimidin-2-yl)-N-methyl methanesulfonamide (i.e. the intermediate compound of formula (I), hereinafter called "compound I") is firstly treated with an alkali, followed by undergoing Wittig reaction with the aldehyde of formula (II) (hereinafter called "compound II") to give the intermediate compound of formula (III) (hereinafter called "compound III").

(2) The intermediate compound of formula (III) undergoes deprotection and hydrolysis reactions sequentially to give the sodium salt intermediate, sodium (E)-7-[4-(4-fluorophenyl)-6-isopropyl-2-[methyl(methylsulfonyl)amino]pyrimidin-5-yl]-(3R,5S)-3,5-dihydroxy-hept-6-enoate (compound IV).

(3) Sodium (E)-7-[4-(4-fluorophenyl)-6-isopropyl-2-[methyl(methylsulfonyl)amino]pyrimidin-5-yl]-(3R,5S)-3,5-dihydroxy-hept-6-enoate (compound IV) is reacted with a calcium salt to give calcium bis[(E)-7-[4-(4-fluorophenyl)-6-isopropyl-2-[methyl(methyl sulfonyl)amino]pyrimidin-5-yl](3R,5S)-3,5-dihydroxy-hept-6-enoate], i.e. rosuvastatin calcium.

The reaction scheme is as follows.

Another aspect of the present application provides a method for preparing rosuvastatin calcium, in which the above intermediate compound of formula (I) is used as a starting material, which firstly undergoes Wittig reaction with the compound of formula (II) to give the intermediate of formula (III), which in turn undergoes deprotection and hydrolysis as well salt formation to give rosuvastatin calcium.

The reaction scheme is as follows:

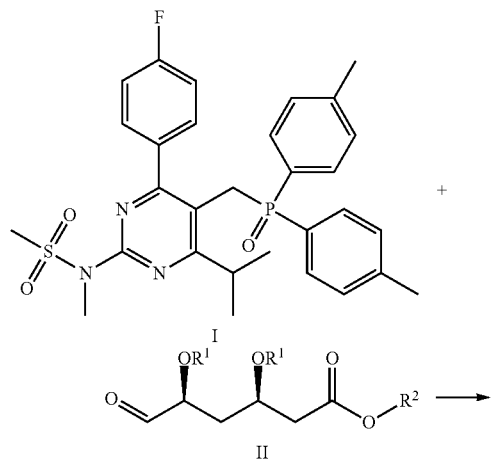

II

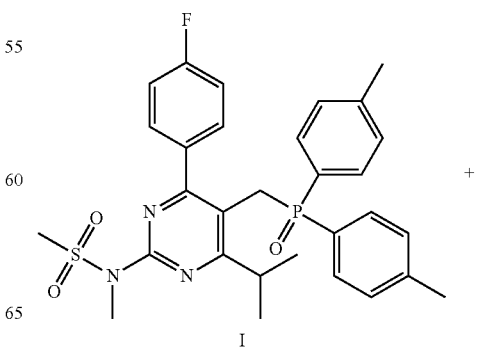

I

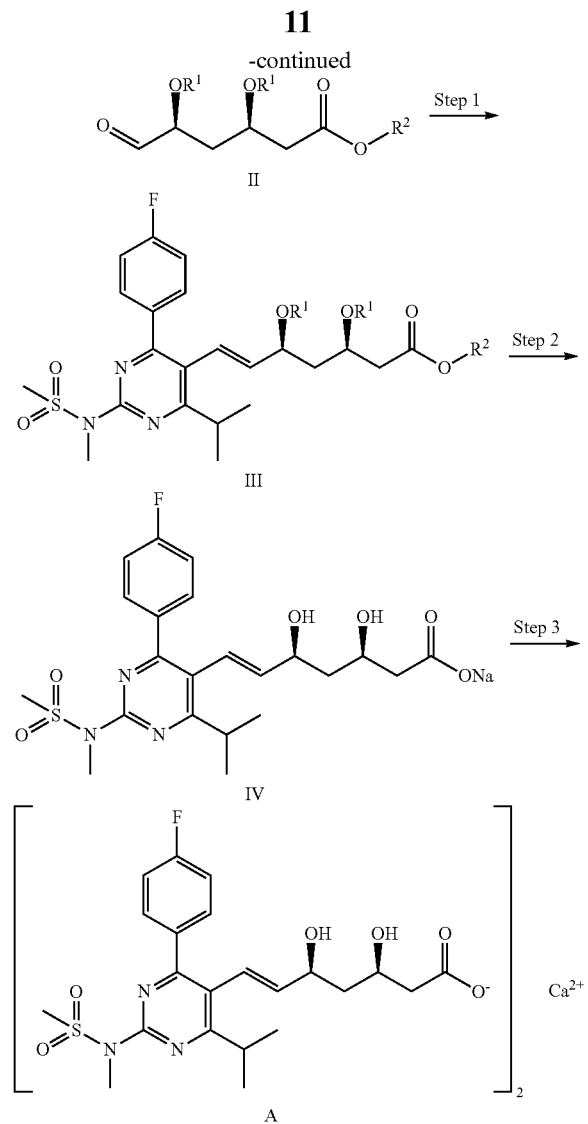

Specifically, the process of step (1) comprises: adding N-(5-(4,4'-tolylphosphono)-methyl)-4-(4-fluorophenyl)-6-isopropylpyrimidin-2-yl)-N-methylmethanesulfonamide to an organic solvent, stirring to clearness, cooling down to −80~−20° C. followed by adding an alkali, stirring for 2 hours while keeping the temperature at −80~−20° C. followed by adding dropwise a solution of the compound of formula (II), reacting at −80~−20° C. for 1~3 hours after the addition is completed, warming up to −45~25° C. and reacting until the reaction is completed, quenching the reaction, extracting the aqueous phase with an organic solvent, combining the organic phase and concentrating, and adding a solvent to the crude product obtained by concentrating, which leads to crystallization to give the intermediate compound of formula (III).

In one embodiment, the molar ratio of compound II to compound I is 1~2:1, preferably 1.2:1. The organic solvent used for dissolving the reactants is selected from the group consisting of 1,4-dioxane, tetrahydrofuran, 2-methyltetrahydrofuran, N,N-dimethylformamide, methyl tert-butyl ether, ethylene glycol dimethyl ether and a mixture of two of them in any ratio, preferably tetrahydrofuran. The amount of the organic solvent is 5~20 mL/g relative to compound I. The alkali used in the reaction is selected from the group consisting of sodium hydride, butyllithium, lithium diisopropylamide, lithium hexamethyldisilazide, sodium hexamethyldisilazide, 2,2,6,6-tetramethylpiperidinylmagnesium chloride, 2,2,6,6-tetramethylpiperidine lithium, potassium hexamethyldisilazide, lithium isopropylphenylamide and sodium isopropylphenylamide; the molar ratio of the alkali to compound I is 0.9~2.0:1, preferably 1.1:1. The solvent for extraction is selected from the group consisting of ethyl acetate, ethyl ether, methyl tert-butyl ether, n-heptane, toluene, dichloromethane and a mixture thereof in any ratio, preferably n-heptane or toluene; and the amount of the solvent for extraction is 5~40 mL/g relative to compound I. The solvent for crystallization is selected from the group consisting of methanol, ethanol and isopropanol, preferably methanol; and the amount of the solvent for crystallization is 2~20 mL/g relative to compound I.

The process of step (2) comprises: adding compound III to an organic solvent, adding an acid after stirring to homogeneity, reacting until compound III is completely consumed, followed by adding an alkaline solution to the reaction system and stirring, monitoring until the dihydroxy ester intermediate is completely consumed, stopping stirring and removing the organic solvent from the reaction system under reduced pressure followed by adding purified water to make the system clear, extracting the aqueous phase 1~3 times with an organic solvent, removing residue organic solvent from the resultant aqueous phase under reduced pressure to give an aqueous solution of compound IV.

In one embodiment, the organic solvent used in the reaction is selected from the group consisting of methanol, ethanol, acetonitrile, isopropanol, acetone and a mixture thereof in any ratio, preferably acetonitrile. The reaction temperature after adding the acid is 10~50° C., preferably 35~40° C. The acid added in the reaction is selected from the group consisting of hydrochloric acid having a mass percentage concentration of 0.02~10%, preferably diluted hydrochloric acid having a mass percentage concentration of 0.06%; and the molar ratio of the added acid to compound III is from 0.001:1 to 5:1, preferably 0.02:1. The reaction time after adding the acid may be 1~24 hours, preferably 4~5 hours. The added alkali is selected from the group consisting of sodium hydroxide, potassium hydroxide, potassium carbonate, sodium carbonate, potassium tert-butoxide and a mixture thereof in any ratio, preferably an aqueous solution of sodium hydroxide having a mass percentage concentration of 4%. The reaction temperature after adding the alkali is 10~50° C., preferably 20~25° C. The molar ratio of the added alkali to compound III is from 0.01:1 to 10:1, preferably 1.1:1. The reaction time after adding the alkali may be 1~24 hours, preferably 6~7 hours. The solvent for extraction in the post-treatment after the reaction is selected from the group consisting of toluene, ethyl acetate, ethyl ether, methyl tert-butyl ether, n-heptane, xylene and a mixture thereof in any ratio, preferably methyl tert-butyl ether.

The process of step (3) comprises: adding dropwise a water-soluble calcium salt to the aqueous solution of sodium (E)-7-[4-(4-fluorophenyl)-6-isopropyl-2-[methyl(methylsulfonyl)amino]pyrimidin-5-yl]-(3R,5S)-3,5-dihydroxyhept-6-enoate (compound IV), reacting for several hours, suctioning, washing the cake once with purified water, suctioning to dryness, drying the cake in vacuum to give rosuvastatin calcium.

In one embodiment, the added water-soluble calcium salt is selected from the group consisting of an aqueous solution of calcium chloride, calcium nitrate and calcium acetate having a mass percentage concentration of 3~20%, preferably an aqueous solution of calcium chloride having a mass percentage concentration of 10%. The molar ratio of the calcium ion in the added calcium salt to compound IV is 0.5~3:1, preferably 0.6:1. The temperature under which the water-soluble calcium salt is added is 20~80° C., preferably 35~45° C. The reaction time after adding the water-soluble calcium salt may be 1~24 hours, preferably 2~3 hours.

In order to sufficiently illustrate the present invention, the preparation method of the present application is verified in the following examples. The examples are provided for exemplary explanation and as specific representatives, and should not be construed or understood as limitations to the scope of the present application.

All the experimental materials in the examples are commercially available unless otherwise indicated. Although the description in the examples of the present application starts from the starting compound, a person skilled in the art would understand that the process of the examples of the present application can start from any intermediate and step in case a certain intermediate product is available.

EXAMPLE 1

Preparation of Compound I

A 2 L four-necked flask charged with 61 g of di(p-tolyl) phosphinate (compound (VII), prepared by referring to *Org. Lett.* 2005, 7, 4277~4280) and 1 L of tetrahydrofuran solution was cooled down to –20° C., followed by adding dropwise 109 mL of butyllithium solution (2.5 M) at the same temperature. After the addition is completed, the mixture was stirred for 30 minutes. A solution comprising N-(5-(bromomethyl)-4-(4-fluorophenyl)-6-isopropylpyrimidin-2-yl)-N-methyl methanesulfonamide (compound V) was then added dropwise while keeping the temperature at –20° C. After the addition is completed, the reaction was continued until the starting materials were completely consumed. The reaction was quenched with 1 L of water. The liquid was separated. The aqueous phase was extracted with 0.5 L of ethyl acetate. The organic phase was combined, and concentrated. The resultant solid was recrystallized in toluene to give compound I with a yield of 87%, and HPLC purity of >99%.

$^1$H NMR (400 MHz, CDCl$_3$) δ: 1.24 (6H, d, J=6.4 Hz), 2.38 (6H, s), 3.42~3.51 (7H, m), 3.87 (2H, d), 6.89~6.93 (2H, m), 7.10~7.16 (6H, m), 7.28~7.32 (4H, m).

EXAMPLE 2

(1) Preparation of tert-butyl 6-[(1E)-2-[4-(4-fluorophenyl)-6-isopropyl-2-[methyl(methane sulfonyl)amino]-5-pyrimidinyl]vinyl]-2,2-dimethyl-1,3-dioxane-4-acetate (compound III)

To a 5 L four-necked flask, 2 L (8 mL/g) of tetrahydrofuran and 250 g (1 mol) of N-(5-((4,4'-tolylphosphono)methyl)-4-(4-fluorophenyl)-6-isopropylpyrimidin-2-yl)-N-methyl methane sulfonamide (compound I) were sequentially added, and stirred to clearness. The mixture was cooled down to –70~–65° C., followed by adding 486.2 mL (1.1 mol, calculated from virtually titrated content) of sodium hexamethyldisilazide. The system was kept at –70~–65° C. for 2 hours, followed by adding dropwise a solution of 132.4 g (1.1 mol) of tert-butyl (4R-cis)-6-formyl-2,2-dimethyl-1,3-dioxane-4-acetate in 500 mL of tetrahydrofuran (2 mL/g). After the addition was completed, the system was stirred at the same temperature for 2 hours, followed by warming up to about 10° C. and reacting until compound I was completely consumed. The reaction system was then quenched with 1 L (4 mL/g) of purified water. The liquid was separated. The aqueous phase was extracted twice with 1.25 L (5 mL/g) of n-heptane. The organic phase was combined, washed with 750 mL (3 mL/g) of saturated brine, and concentrated to dryness. To the concentrated system was added 500 mL (2 mL/g) of methanol, leading to crystallization to give compound III with a purity of about 98%, a stereo-selectivity of E/Z=99.8:0.2, and a yield of 82%.

$^1$H NMR (400 MHz, CDCl$_3$) δ: 0.88 (t, J=7.4 Hz, 3H); 1.09~1.25 (m, 7H); 1.39~1.52 (m, 13H); 1.77 (q, J=7.3 Hz, 2H); 2.30 (dd, J$_1$=15.1 Hz, J$_2$=5.9 Hz, 1H); 2.45 (dd, J$_1$=15.3 Hz, J$_2$=7.0 Hz, 1H); 3.35~3.39 (m, 1H); 3.51 (s, 3H); 3.56 (s, 3H); 4.28 (br, 1H); 4.41~4.43 (br, 1H); 5.46 (dd, J$_1$=16.2 Hz, J$_2$=5.0 Hz, 1H); 6.51 (d, J=16.3 Hz, 1H); 7.05~7.09 (m, 2H); 7.63~7.66 (m, 2H); HRMS (ESI) calculated: C$_{30}$H$_{42}$FN$_3$O$_6$S; [M+1H]$^+$=592.28, determined: 592.3.

(2) Preparation of sodium (E)-7-[4-(4-fluorophenyl)-6-isopropyl-2-[methyl(methylsulfonyl) amino]pyrimidin-5-yl]-(3R,5S)-3,5-dihydroxy-hept-6-enoate (compound IV)

To a 5 L four-necked flask, 2 L (10 mL/g) of acetonitrile and 200 g (1 mol) of tert-butyl 6-[(1E)-2-[4-(4-fluorophenyl)-6-isopropyl-2-[methyl(methanesulfonyl)amino]-5-pyrimidinyl]vinyl]-2,2-dimethyl-1,3-dioxane-4-acetate (compound III) were added, and stirred to homogeneity, followed by adding 14.8 g (0.02 mol, calculated from titrated content) of an aqueous solution of hydrochloric acid having a mass percentage concentration of 0.06%. The system was warmed up to 35° C. and stirred at the same temperature for 5 hours until compound III was completely consumed. To the reaction system was added dropwise 32.5 g (1.1 mol) of an aqueous solution of sodium hydroxide having a mass percentage concentration of 4%, and stirred at 20° C. for 7 hours until the dihydroxy ester intermediate produced in the first phase was completely consumed. The system was concentrated to remove acetonitrile, followed by adding 2 L (10 mL/g) of purified water, and stirred to clearness. The system was extracted three times with 400 mL (2 mL/g) of methyl tert-butyl ether. The aqueous phase was further concentrated until no organic solvent was left, to give the an aqueous solution of the product, sodium (E)-7-[4-(4-fluorophenyl)-6-isopropyl-2-[methyl(methylsulfonyl)amino]pyrimidin-5-yl]-(3R,5S)-3,5-dihydroxy-hept-6-enoate (compound IV), with a purity of >98% and a yield of 97%.

(3) Preparation of Rosuvastatin Calcium (Compound A)

To a 5 L four-necked flask containing 200 g (1 mol) of the aqueous solution of sodium (E)-7-[4-(4-fluorophenyl)-6-isopropyl-2-[methyl(methylsulfonyl)amino]pyrimidin-5-yl]-(3R,5S)-3,5-dihydroxy-hept-6-enoate (compound IV), 52.9 g (1.2 mol) of an aqueous solution of calcium chloride having a mass percentage concentration of 5% was added dropwise. After the addition was completed, the system was warmed up to 35° C., and stirred at the same temperature for 3 hours. After suctioning, the cake was beaten up with 2 L (10 mL/g) of purified water. The mixture was suctioned to dryness and the cake was dried in vacuum to give rosuvastatin calcium with an HPLC purity of >99.5% and a yield of 87%.

$^1$H NMR (400 MHz, d$_6$-DMSO) δ: 1.20 (d, J=6.0 Hz, 12H); 1.34 (br, 2H); 1.52 (br, 2H); 2.05 (br, 2H); 2.16 (br,

2H); 3.41~3.44 (br, 10H); 3.53 (s, 6H); 3.82~3.88 (br, 2H); 4.22 (br, 2H); 5.07 (br, 2H); 5.52 (dd, $J_1$=16.0 Hz, $J_2$=5.8 Hz, 2H); 6.52 (d, J=16.2 Hz, 2H); 7.23~7.27 (m, 4H); 7.70 (br, 4H). HRMS (ESI) calculated: $C_{44}H_{54}CaF_2N_6O_{12}S_2$; [M+1H]+=482.17, determined: 482.1.

EXAMPLE 3

(1) Preparation of tert-butyl 6-[(1E)-2-[4-(4-fluorophenyl)-6-isopropyl-2-[methyl(methane sulfonyl) amino]-5-pyrimidinyl]vinyl]-3,5-bis(tert-butyldimethylsiloxy)-hexanoate To a 5 L four-necked flask, 1.6 L (8 mL/g) of 2-methyltetrahydrofuran and 200 g (1 mol) of N-(5-((4,4'-tolylphosphono)-methyl)-4-(4-fluorophenyl)-6-isopropyl pyrimidin-2-yl)-N-methyl methane sulfonamide (compound I) were sequentially added, stirred to clearness, cooled down to −30° C., followed by adding 1.1 mol of lithium isopropylphenylamide. The system was kept at −55° C. for 2 hours, followed by adding dropwise a solution of 173.8 g (1.1 mol) of tert-butyl (3R,5S)-3,5-bis(tert-butyldimethylsiloxy)-6-oxo-hexanoate in 400 mL (2 mL/g) of 2-methyl tetrahydrofuran. After the addition was completed, the system was stirred at the same temperature for 3 hours, followed by warming up to −15° C. and reacting until compound I was completely consumed. The reaction system was then quenched with 800 mL (4 mL/g) of purified water. The liquid was separated. The aqueous phase was extracted twice with 1 L (5 mL/g) of n-heptane. The organic phase was combined, washed with 600 mL (3 mL/g) of saturated brine, and concentrated to dryness. To the concentrated system was added 1 L (5 mL/g) of methanol, leading to crystallization to give compound III with a purity of 99%, a stereo-selectivity of E/Z=99.7:0.3, and a yield of 77%.

$^1$H NMR (400 MHz, CDCl$_3$) δ: −0.41 (s, 6H); −0.36 (s, 6H); 0.83 (s, 9H); 0.91 (s, 9H); 1.19~1.21 (m, 15H); 1.31 (m, 1H); 1.57 (br, 1H); 2.03~2.06 (br, 1H); 2.17 (br, 1H); 3.42 (m, 1H); 3.54 (s, 3H); 3.67 (s, 3H); 3.89~3.91 (m, 1H); 4.20 (br, 1H); 5.53 (dd, J1=16.0 Hz, J2=5.8 Hz, 1H); 6.53 (d, J=15.8 Hz, 1H); 7.21~7.25 (m, 2H); 7.76~7.78 (m, 2H). HRMS (ESI) calculated: $C_{38}H_{64}FN_3O_6SSi_2$; [M+1H]$^+$=766.40, determined 766.4.

(2) Preparation of sodium (E)-7-[4-(4-fluorophenyl)-6-isopropyl-2-[methyl(methylsulfonyl) amino]pyrimidin-5-yl]-(3R,5S)-3,5-dihydroxy-hept-6-enoate (compound IV)

To a 2 L four-necked flask, 1.6 L (8 mL/g) of acetonitrile and 100 g (1 mol) of tert-butyl 6-[(1E)-2-[4-(4-fluorophenyl)-6-isopropyl-2-[methyl(methanesulfonyl)amino]-5-pyrimidinyl]vinyl]-3,5-bis(tert-butyldimethylsiloxy)-hexanoate (compound III) were added, stirred to homogeneity, followed by adding an aqueous solution of 14.8 g (0.03 mol, calculated from titrated content) of hydrochloric acid having a mass percentage concentration of 0.09%. The system was warmed up to 40° C., and stirred at the same temperature for 4 hours until compound III was completely consumed. To the reaction system was added dropwise an aqueous solution of 11.0 g (1.1 mol) of sodium hydroxide having a mass percentage concentration of 4%, stirred for 2.5 hours, until the dihydroxy ester intermediate produced in the first phase was completely consumed. The system was concentrated to remove acetonitrile, followed by adding 2 L (10 mL/g) of purified water, and stirred to clearness. The system was extracted three times with 300 mL (3 mL/g) of methyl tert-butyl ether. The aqueous phase was further concentrated until no organic solvent was left, to give an aqueous solution of the product, sodium (E)-7-[4-(4-fluorophenyl)-6-isopropyl-2-[methyl(methylsulfonyl)amino]pyrimidin-5-yl]-(3R, 5S)-3,5-dihydroxy-hept-6-enoate (compound IV), with a purity of >97% and a yield of 85%.

(3) Preparation of Rosuvastatin Calcium (Compound A)

To a 1 L four-necked flask containing an aqueous solution of 50 g (1 mol) of sodium (E)-7-[4-(4-fluorophenyl)-6-isopropyl-2-[methyl(methylsulfonyl)amino]pyrimidin-5-yl]-(3R,5S)-3,5-dihydroxy-hept-6-enoate (compound IV), 8.6 g (0.55 mol) of an aqueous solution of calcium acetate having a mass percentage concentration of 5% was added dropwise. After the addition was completed, the system was warmed up to 40° C., and stirred at the same temperature for 5 hours. After suctioning, the cake was beaten up with 2 L (10 mL/g) of purified water. The mixture was suctioned to dryness and the cake was dried in vacuum to give rosuvastatin calcium with an HPLC purity of >99.5% and a yield of 82%.

EXAMPLE 4

(1) Preparation of cyclopentyl 6-[(1E)-2-[4-(4-fluorophenyl)-6-isopropyl-2-[methyl (methane sulfonyl) amino]-5-pyrimidinyl]vinyl]-2,2-dimethyl-1,3-dioxane-4-acetate (compound III)

To a 5 L four-necked flask, 2.5 L (10 mL/g) of N,N-dimethylformamide and 250 g (1 mol) of N-(5-((4,4'-tolylphosphono)-methyl)-4-(4-fluorophenyl)-6-isopropylpyrimidin-2-yl)-N-methyl methanesulfonamide (compound I) were sequentially added, and stirred to clearness. The mixture was cooled down to −40° C., followed by adding 12.7 g (1.2 mol, calculated from virtual content) of sodium hydride. The system was kept at −40° C. and stirred for 2 hours, followed by adding dropwise a solution of 143.4 g (1.2 mol) of cyclopentyl (4R-cis)-6-formyl-2,2-dimethyl-1, 3-dioxane-4-acetate in N,N-dimethylformamide. After the addition was completed, the system was further stirred for 5 hours, until compound I was completely consumed. The reaction system was then quenched with 250 L (1 mL/g) of purified water. The liquid was separated. The aqueous phase was extracted twice with 1.25 L (5 mL/g) of n-heptane. The organic phase was combined, washed with 750 mL (3 mL/g) of saturated brine, and concentrated to dryness. To the concentrated system was added 750 mL (3 mL/g) of methanol, leading to crystallization to give compound III with a purity of 94%, a stereo-selectivity of E/Z=99:1, and a yield of 67%. In order to improve the purity of the product, the product was recrystallized from 3 mL/g of methanol before being used in the next step.

$^1$H NMR (400 MHz, CDCl$_3$) δ: 1.26 (dd, $J_1$=6.5 Hz, $J_2$=3.0 Hz, 6H), 1.39 (s, 3H), 1.45-1.54 (m, 2H), 1.48 (s, 3H), 1.55-1.62 (m, 2H), 1.66-1.76 (m, 4H), 1.80-1.90 (m, 2H), 2.34 (dd, $J_1$=15.3 Hz, $J_2$=5.9 Hz, 1H), 2.49 (dd, $J_1$=15.3 Hz, $J_2$=7.1 Hz, 1H), 3.34-3.41 (m, 1H), 3.51 (s, 3H), 3.56 (s, 3H), 4.27-4.35 (m, 1H), 4.40-4.46 (m, 1H), 5.16-5.21 (m, 1H), 5.47 (dd, $J_1$=16.2 Hz, $J_2$=5.2 Hz, 1H), 6.52 (d, J=16.2 Hz, 1H), 7.08 (t, J=8.5 Hz, 2H), 7.65 (dd, $J_1$=8.5 Hz, $J_2$=5.6 Hz, 2H). HRMS (ESI) calculated: $C_{30}H_{40}FN_3O_6S$; [M+1H]$^+$=590.26, determined: 590.3.

(2) Preparation of sodium (E)-7-[4-(4-fluorophenyl)-6-isopropyl-2-[methyl(methylsulfonyl) amino] pyrimidin-5-yl]-(3R,5S)-3,5-dihydroxy-hept-6-enoate (compound IV)

To a 1 L four-necked flask, 500 mL (10 mL/g) of methanol and 50 g (1 mol) of cyclopentyl 6-[(1E)-2-[4-(4-fluorophenyl)-6-isopropyl-2-[methyl(methanesulfonyl)amino]-5-pyrimidinyl]vinyl]-2,2-dimethyl-1,3-dioxane-4-acetate (compound III) were added, and stirred to homogeneity, followed by adding 3.7 g (1.2 mol, calculated from titrated content) of an aqueous solution of hydrochloric acid having a mass percentage concentration of 3%, and stirring until compound III was completely consumed. To the reaction system was added dropwise 8.1 g (2.4 mol) of an aqueous solution of sodium hydroxide having a mass percentage concentration of 8%. After the addition was completed, the system was warmed up to 45° C., and stirred for 3 hours, until the dihydroxy ester intermediate produced in the first phase was completely consumed. The system was concentrated to remove methanol, followed by adding 500 mL (10 mL/g) of purified water, and stirred to clearness. The system was extracted once with 250 mL (5 mL/g) of methyl tert-butyl ether. The aqueous phase was further concentrated until no organic solvent was left, to give an aqueous solution of the product, sodium (E)-7-[4-(4-fluorophenyl)-6-isopropyl-2-[methyl(methyl sulfonyl)amino]pyrimidin-5-yl]-(3R,5S)-3,5-di hydroxy-hept-6-enoate (compound IV), with a purity of >98% and a yield of 89%.

(3) Preparation of Rosuvastatin Calcium (Compound A)

To a 1 L four-necked flask containing 50 g (1 mol) of the aqueous solution of sodium (E)-7-[4-(4-fluorophenyl)-6-isopropyl-2-[methyl(methyl sulfonyl)amino]pyrimidin-5-yl]-(3R,5S)-3,5-dihydroxy-hept-6-enoate (compound IV), 9.4 g (0.6 mol) of an aqueous solution of calcium acetate having a mass percentage concentration of 5% was added dropwise. After the addition was completed, the system was warmed up to 35° C., and stirred at the same temperature for 16 hours. After suctioning, the cake was beaten up with 2 L (10 mL/g) of purified water. The mixture was suctioned to dryness and the cake was dried at 50° C. to give rosuvastatin calcium with an HPLC purity of >99.5% and a yield of 83%.

EXAMPLE 5

(1) Preparation of cyclohexyl 6-[(1E)-2-[4-(4-fluorophenyl)-6-isopropyl-2-[methyl(methane sulfonyl) amino]-5-pyrimidinyl]vinyl]-2,2-dim ethyl-1,3-dioxane-4-acetate (compound III)

To a 2 L four-necked flask, 800 mL (8 mL/g) of 2-methyl tetrahydrofuran and 100 g (1 mol) of N-(5-((4,4'-tolyl-phosphono)-methyl)-4-(4-fluorophenyl)-6-isopropylpyrimidin-2-yl)-N-methyl methanesulfonamide (compound I) were sequentially added, and stirred to clearness. The mixture was cooled down to −50° C., followed by adding 1.4 mol of 2,2,6,6-tetramethylpiperidine lithium. The system was kept at −50° C. and stirred for 2 hours, followed by adding dropwise a solution of 132.4 g (1.1 mol) of cyclohexyl (4R-cis)-6-formyl-2,2-dimethyl-1,3-dioxane-4-acetate in 200 mL (2 mL/g) of 2-methyltetrahydrofuran. After the addition was completed, the system was further stirred at the same temperature for 2 hours, followed by warming up to −20° C. and further stirring until compound I was completely consumed. The reaction system was then quenched with 400 mL of water. The liquid was separated. The aqueous phase was extracted three times with 1 L (10 mL/g) of n-heptane. The organic phase was combined, washed sequentially with 200 mL (2 mL/g) of purified water and 300 mL (3 mL/g) of saturated brine, and concentrated to dryness in vacuum. To the concentrated system was added 500 mL (5 mL/g) of methanol for washing to give compound III with a purity of 98.5%, a stereo-selectivity of E/Z=99.8: 0.2, and a yield of 86%.

$^1$H NMR (400 MHz, CDCl$_3$) δ: 1.26 (dd, J$_1$=6.6 Hz, J$_2$=2.8 Hz, 6H), 1.33~1.56 (m, 8H), 1.36 (s, 3H), 1.45 (s, 3H), 1.67~1.75 (m, 2H), 1.78~1.86 (m, 2H), 2.36 (dd, J$_1$=15.3 Hz, J$_2$=5.9 Hz, 1H), 2.50 (dd, J$_1$=15.2 Hz, J$_2$=7.0 Hz, 1H), 3.34~3.40 (m, 1H), 3.50 (s, 3H), 3.56 (s, 3H), 4.27~4.35 (m, 1H), 4.40~4.46 (m, 1H), 4.74~4.82 (m, 1H), 5.46 (dd, J$_1$=16.2 Hz, J$_2$=5.3 Hz, 1H), 6.52 (d, J=16.2 Hz, 1H), 7.07 (t, J=8.6 Hz, 2H), 7.64 (dd, J$_1$=8.6 Hz, J$_2$=5.5 Hz, 2H). HRMS (ESI) calculated: C$_{31}$H$_{42}$FN$_3$O$_6$S; [M+1H]+=604.28, determined: 604.3.

(2) Preparation of sodium (E)-7-[4-(4-fluorophenyl)-6-isopropyl-2-[methyl(methylsulfonyl) amino] pyrimidin-5-yl]-(3R,5S)-3,5-dihydroxy-hept-6-enoate (compound IV)

To a 1 L four-necked flask, 500 mL (10 mL/g) of methanol and 50 g (1 mol) of cyclohexyl 6-[(1E)-2-[4-(4-fluorophenyl)-6-isopropyl-2-[methyl(methanesulfonyl)amino]-5-pyrimidinyl]vinyl]-2,2-dimethyl-1,3-dioxane-4-acetate (compound III) were added, and stirred to homogeneity, followed by adding 14.8 g (0.02 mol, calculated from titrated content) of an aqueous solution of hydrochloric acid having a mass percentage concentration of 0.06%. The system is warmed up to 40° C. and stirred at the same temperature for 4 hours, until compound III was completely consumed. To the reaction system was added dropwise 26 g (1.1 mol) of an aqueous solution of sodium hydroxide having a mass percentage concentration of 5%, and stirred at 25° C. for 7 hours, until the dihydroxy ester intermediate produced in the first phase was completely consumed. The system was concentrated to remove acetonitrile, followed by adding 2 L (10 mL/g) of purified water, and stirred to clearness. The system was extracted three times with 400 mL (2 mL/g) of methyl tert-butyl ether. The aqueous phase was further concentrated until no organic solvent was left, to give an aqueous solution of the product, sodium (E)-7-[4-(4-fluorophenyl)-6-isopropyl-2-[methyl(methylsulfonyl)amino]pyrimidin-5-yl]-(3R,5S)-3,5-dihydroxy-hept-6-enoate (compound IV) with a purity of >99%, and a yield of 94%.

(3) Preparation of Rosuvastatin Calcium (Compound A)

To a 1 L four-necked flask containing 50 g (1 mol) of the aqueous solution of sodium (E)-7-[4-(4-fluorophenyl)-6-isopropyl-2-[methyl(methyl sulfonyl)amino]pyrimidin-5-yl]-(3R,5S)-3,5-dihydroxy-hept-6-enoate (compound IV), 13.2 g (1.2 mol) of an aqueous solution of calcium chloride having a mass percentage concentration of 5% was added dropwise. After the addition was completed, the system was warmed up to 60° C., and stirred at the same temperature for 3 hours. After suctioning, the cake was beaten up with 2 L (10 mL/g) of purified water. The mixture was suctioned to dryness and the cake was dried in vacuum to give rosuvastatin calcium with an HPLC purity of >99%, and a yield of 91%.

Although preferable embodiments of the present application are disclosed in order to illustrate the present application, a person skilled in art should understand that various modifications, additions and replacements can be made to the present application without departing from the concept and scope of the present application as defined by the Claims.

The invention claimed is:
1. An intermediate compound for preparing rosuvastatin calcium, having a structure of formula (I):

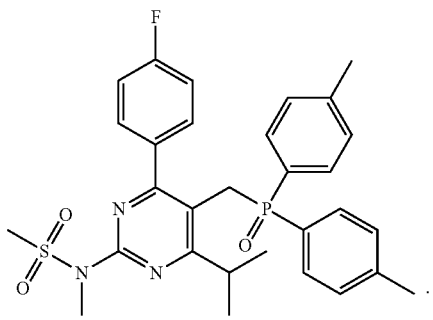

2. A method for preparing rosuvastatin calcium,
the method comprising combining formula (I) with formula (II) to give the intermediate compound formula (III),

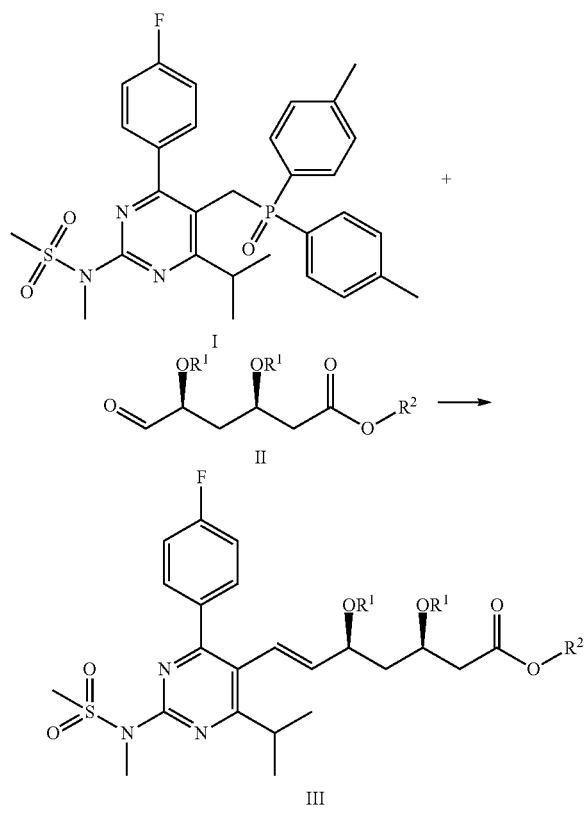

deprotecting and hydrolyzing formula (III) followed by salt formation to give said rosuvastatin calcium:

wherein $R^1$ is selected from TBS, TES or TIPS protecting group, or two $OR^1$ groups form a structure of

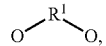

in which $R^1$ is isopropyl; and $R^2$ is C4 to C10 alkyl, cyclopentyl, or cyclohexyl.

3. The method according to claim 2, wherein $R^2$ is tert-butyl, tert-pentyl, cyclopentyl or cyclohexyl.

4. The method according to claim 2, wherein the step of combining formula (I) with formula (II) comprises: adding the intermediate compound formula (I) into an organic solvent, cooling down to −80 to −20° C., then adding an alkali, adding dropwise a solution of formula (II) at −80 to −20° C., reacting at −80 to −20° C. for 1 to 3 hours after the addition is completed, warming up to −45 to 25° C. and reacting until the reaction is completed, quenching the reaction, extracting, concentrating the extraction solution, and adding a solvent to the crude product obtained by concentrating, and crystallizing formula (III).

5. The method according to claim 4, wherein the alkali is selected from the group consisting of sodium hydride, butyllithium, lithium diisopropylamide, lithium hexamethyldisilazide, sodium hexamethyldisilazide, 2,2,6,6-tetramethylpiperidinylmagnesium chloride, 2,2,6,6-tetramethylpiperidine lithium, potassium hexamethyldisilazide, lithium isopropylphenylamide and sodium isopropylphenylamide; and the molar ratio of the alkali to the intermediate compound of formula (I) is from 0.9:1 to 2:1.

6. The method according to claim 4, wherein the organic solvent is selected from the group consisting of 1,4-dioxane, tetrahydrofuran, 2-methyltetrahydrofuran, N,N-dimethylformamide, methyl tert-butyl ether, ethylene glycol dimethyl ether and a mixture of two of them in any ratio; and the amount of the organic solvent is 5~20 mL/g relative to the intermediate compound of formula (I).

7. The method according to claim 4, wherein the molar ratio of the intermediate compound of formula (I) to the compound of formula (II) is 1:2 to 1:1.

8. The method according to claim 4, wherein the solvent for extraction is selected from the group consisting of ethyl acetate, ethyl ether, methyl tert-butyl ether, n-heptane, toluene, dichloromethane, and a mixture thereof in any ratio; and the amount of the solvent is 5~40 mL/g relative to the intermediate compound of formula (I).

9. The method according to claim 4, wherein the solvent for crystallization is selected from the group consisting of methanol, ethanol and isopropanol; and the amount of the solvent is 2~20 mL/g relative to the intermediate compound of formula (I).

10. The method according to claim 2, wherein the deprotecting step comprises adding an acid to formula (III) to conduct the deprotection reaction, the hydrolysis step comprises adding an alkali to give formula (IV), the alkali being selected from the group consisting of an aqueous solution of sodium hydroxide, potassium hydroxide, potassium carbonate, sodium carbonate, potassium tert-butoxide, and a mixture thereof in any ratio, and adding a calcium salt to the compound of formula (IV) to conduct the salt formation reaction to give rosuvastatin calcium:

IV
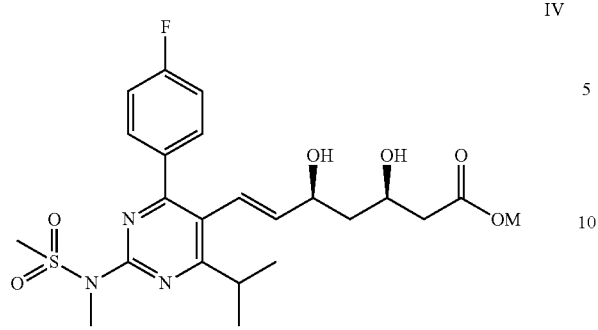
wherein M is Na or K.
* * * * *